(12) United States Patent  
Murphy et al.

(10) Patent No.: US 8,779,230 B2  
(45) Date of Patent: Jul. 15, 2014

(54) SYSTEM AND METHOD FOR TREATING LEG ULCERS

(75) Inventors: Thomas S. Murphy, Boxford, MA (US); Khaled El-Tahlawy, Portsmouth, NH (US)

(73) Assignee: Andover Healthcare, Inc., Salisbury, NH (US)

( * ) Notice: Subject to any disclaimer, the term of this patent is extended or adjusted under 35 U.S.C. 154(b) by 75 days.

(21) Appl. No.: 13/614,075

(22) Filed: Sep. 13, 2012

(65) Prior Publication Data

US 2013/0085435 A1 Apr. 4, 2013

Related U.S. Application Data

(60) Provisional application No. 61/540,727, filed on Sep. 29, 2011.

(51) Int. Cl.
*A61F 13/00* (2006.01)

(52) U.S. Cl.
USPC .................................. 602/48; 602/41; 602/46

(58) Field of Classification Search
CPC ......... A61F 13/00; A61F 13/02; A61F 13/06; A61F 13/08; A61F 13/061; A61F 15/425; A61F 15/26; A61F 15/28
USPC .............. 602/41–42, 46, 48, 74–76; 424/443, 424/444
See application file for complete search history.

(56) References Cited

U.S. PATENT DOCUMENTS

| | | | |
|---|---|---|---|
| 3,872,862 A | 3/1975 | Hume | |
| 7,071,164 B2 | 7/2006 | Quirk et al. | |
| 7,507,870 B2 * | 3/2009 | Nielsen et al. | 602/58 |
| 2002/0099318 A1 | 7/2002 | Suehr et al. | |
| 2007/0237812 A1 | 10/2007 | Patel et al. | |
| 2007/0299383 A1 | 12/2007 | Murphy et al. | |

OTHER PUBLICATIONS

Fonder et al., "Treating the chronic wound; A practical approach to the care of nonhealing wounds and wound care dressings," J. Am. Acad. Dermatol., vol. 58 (2), pp. 185-205 (2008).
International Search Report and Written Opinion dated Nov. 20, 2012, received in PCT/US2012/055089.
D.D.I. Wright et al., "The Function of Multiple Layer Compression Bandaging in the Management of Venous Ulcers," Swiss Med., vol. 10, No. 4a, pp. 109-110 (1988).
iData Research, Inc., "Unna Boot Market," pp. 201-210 (2010).

* cited by examiner

*Primary Examiner* — Kim M Lewis
(74) *Attorney, Agent, or Firm* — McLane, Graf, Raulerson & Middleton, Professional Association (57) ABSTRACT

In one aspect, a wound treatment system includes an inner layer comprising a foam material impregnated with a zinc oxide containing composition with or without calamine and/or ichthammol and in the presence or absence of antimicrobial agent (inorganic and/or organic). An optional outer layer comprises a short/long stretch compression bandage. In another aspect, a method of manufacturing the foam article impregnated with the zinc oxide containing composition is disclosed. In yet another aspect, a method of applying the wound treatment system to a patient's leg is disclosed. In still another aspect, a kit is provided including a foam layer impregnated with a zinc oxide containing composition; optionally, an elastic bandage component (e.g., long or short stretch elastic bandage); and, optionally, an outer stocking or sleeve, wherein the bandage system components are packaged together.

31 Claims, 13 Drawing Sheets

SYSTEM AND METHOD FOR TREATING LEG ULCERS

CROSS REFERENCE TO RELATED APPLICATION

This application claims the priority benefit of U.S. Provisional Application No. 61/540,727 filed Sep. 29, 2011. The aforementioned application is incorporated herein by reference in its entirety.

BACKGROUND

The present disclosure relates generally to a wound care bandaging system and, more particularly, to a system and method for the treatment of leg ulcers. The system and method of the present disclosure may advantageously be used in the treatment of venous stasis ulcers, e.g., caused by venous valve insufficiency, venous wall damage, and so forth, and will be described herein primarily by way of reference thereto. However, it will be recognized that the present bandaging system will also find utility in the treatment of edema, eczema, ulcers, and other wounds or sores of the lower extremities having various origins.

It is well known in the art to apply a dressing known as an "Unna boot" or alternatively "Unna's boot" for the treatment of venous stasis ulcers and other venous insufficiencies of the leg. An Unna boot is a gauze bandage, typically a 3-4 inch wide woven cotton gauze or scrim coated with a medicated zinc paste, sometimes referred to as "Unna's paste," which comprises zinc oxide in a carrier of glycerin and/or gelatin, and may also contain other ingredients such as calamine (e.g., zinc oxide, zinc carbonate, or zinc silicate, colored with ferric oxide), methyl paraben, propyl paraben, acacia, castor oil, white petrolatum, ichthammol, and so forth. Unna boots were brought to market in 1904, one hundred and eight years ago, and have remained essentially unchanged. Unna boot bandages are currently widely commercially available from a variety of manufacturers and distributors, including BSN Medical, Inc., Bayer Pharmaceuticals Corporation, Covidien AG, and others.

In use, the Unna boot is typically applied by wrapping the paste-impregnated gauze under light tension in spiral, overlapping turns starting at the base of the toes and stopping 1-2 inches below the knee. The gauze is typically covered with an outer layer such as an elastic or cohesive bandage, dry gauze, tubular bandage, stocking or sock which may be provided to provide additional compression to the leg as well as to protect the paste bandage and to keep the patient's clothing clean. Unna boots can sometimes be left on for up to 7 days before changing. However, because the prior art Unna boot cannot absorb a large volume of fluid, frequent changing is required when applied to large, severe, and/or heavily draining ulcers, for example, when drainage from the wound starts to leak from the Unna boot dressing.

Commonly, absorbent pads (e.g., formed of cotton or cotton/wool batting material) are applied to the inside of the impregnated gauze layer covering the area of the ulcer to absorb excess exudate. However, even with absorbent pads, seepage of the wound exudate throughout the wrap is common. Exudate, which resembles blood plasma in composition, contains a variety of substances including inflammatory mediators and protein-digesting enzymes, among other things, which can have a damaging effect on both the wound being treated as well as healthy skin that is otherwise undamaged by the wound or ulcer being treated.

In addition, the presence of one or more additional absorbent layers increases the time required to apply the bandage system. It also decreases patient comfort because the additional thickness makes such three (or more) layer systems more difficult to wear under clothing and footwear and causes the uncomfortable buildup of body heat and moisture under the bandages. The additional time to apply such prior art bandage systems, the increased thickness of such three or more layered systems, and the increased patient discomfort, in turn, reduce patient compliance.

Another drawback of the prior art Unna boot resides in the inability to provide a uniform coating of the zinc oxide paste on the woven gauze. As can be seen in FIG. 6 and FIGS. 11A-11D, the prior art gauze has some areas where the paste is heavily applied and other areas where the paste is extremely thinly applied. Given the inability of the woven gauze materials to hold a consistent uniformity of paste, the portion of the gauze dressing that contacts the skin being treated will often lack an adequate amount of the zinc oxide paste. The lack of uniformity of the medicated paste can also result in a lack of paste in the region of the wound being treated and/or excess paste in regions of healthy skin where it is not needed. Because the gauze layer is applied by overlapping consecutive turns of the dressing, e.g., by about 50-75%, it is possible to achieve an overall appearance of uniformity. However, such appearance of uniformity occurs as a result of multiple overlapping layers. For example, the Unna boot gauze dressing is typically applied using a simple, overlapping spiral technique, e.g., using a 50-75% overlap on adjacent turns. In such cases, only 25-50% of each turn contacts the patient's skin. Given the highly random and splotchy coverage of the Unna paste in the prior art Unna boot gauze dressings, much of the Unna paste giving the appearance of uniform coverage is actually separated from the patient's skin by one or more layers of the dressing, where it will not be delivered to the affected skin area of the wound being treated.

The present disclosure provides a new and greatly improved wound care bandage system and method which overcome the above-referenced problems and others.

SUMMARY

In the course of describing the system and method of this disclosure below, unless specifically stated otherwise, the term zinc oxide containing composition is intended to include any composition containing zinc oxide as an active ingredient and which is suitable for impregnating the foam bandage layer herein. The zinc oxide containing compositions herein may optionally include calamine, ichthammol, or both as additional active ingredients. Still further additives to the zinc oxide containing compositions are discussed in greater detail below. In addition, the zinc oxide containing compositions may optionally include an antimicrobial agent and/or may be used in the presence of or the absence of an antimicrobial agent. If an antimicrobial agent is present, either as a part of the zinc oxide containing composition or as a separately applied antimicrobial agent or formula, such antimicrobial agent may be any antimicrobial agent suitable for topical administration, including organic or inorganic antimicrobial agents. Terms such as elastic bandage, elastic layer, compression bandage, compression layer, and similar terms are intended to encompass both short stretch bandages and long stretch bandages unless specifically stated otherwise.

In one aspect of the present disclosure, a wound care bandage system includes a skin-contacting layer comprising a foam layer impregnated with a zinc oxide containing composition. In a further, more limited aspect, an optional second layer comprising an elastic bandage may be disposed over the first, skin-contacting layer.

In another aspect of the present development, a wound care kit includes components packaged together, the components comprising a first, skin-contacting layer comprising a foam layer impregnated with a zinc oxide containing composition and a second layer disposed over the first layer comprising an elastic bandage.

In yet another aspect, a method of treating a skin ulcer in the leg of a patient comprises wrapping the leg with a wound dressing comprising a foam layer impregnated with a zinc oxide paste. A second, elastic bandage layer may be wrapped over the impregnated foam layer.

One advantage of the wound care bandage system and method of the present disclosure resides in the ability to provide a uniform coating of the zinc oxide containing composition on the foam layer and to thereby deliver the correct level of medication to the area to be treated.

Another advantage of the present disclosure resides in its ability to absorb large amounts of wound exudate.

Another advantage of the present bandage system herein resides in its increased conformity to the legs/lower extremity of the user. Specifically, the present system has the ability to conform to virtually all sizes and shapes without gaps or loose material to cut or fold.

Another advantage of the present system is that it is easier, quicker, and less messy to apply than prior art Unna Boot products. The ease of use, in turn, results in increased patient compliance.

Still another advantage of the present development is found in improved wound healing and control of edema as compared to the prior art Unna Boot systems.

Yet another advantage of the present system is that it does not adhere to the patient's leg.

Still another advantage of the present invention resides in the fact that a stretchable or elastic foam impregnated with a zinc oxide containing composition may be employed, thus providing a degree of compression to the limb being treated.

Still further advantages and benefits of the present system and method will become apparent to those of ordinary skill in the art upon reading and understanding the following detailed description of the preferred embodiments.

DETAILED DESCRIPTION OF THE PREFERRED EMBODIMENTS

In general, embodiments of the invention provide a medicated bandage system, including an inner layer comprising a foam material, and an optional outer layer comprising a separate short or long stretch compression bandage. The inner foam layer is impregnated with a zinc oxide containing composition.

The zinc oxide containing composition preferably comprises from about 5% to about 40% by weight of zinc oxide and more preferably from about 10% to about 20% by weight of zinc oxide. The zinc oxide containing composition may additionally comprise additional active ingredients such as calamine and/or ichthammol. The zinc oxide containing composition preferably comprises from about 0% to about 10% by weight of calamine and/or ichthammol and in certain embodiments may contain from about 1% to about 5% by weight of calamine and/or ichthammol.

By way of non-limiting example, in certain embodiments, the foam layer may be impregnated with a zinc oxide containing composition containing zinc oxide, calamine, water, glycerin, gelatin, sorbitol, magnesium aluminum silicate, and Paraben-DU.

The choice of foam for the inner layer is useful in many respects. For example, the foam material is elastic and can be wrapped under light tension to provide an initial degree of compression. In addition, the foam layer has been found to be far superior in absorbing wound exudate as compared to the prior art cotton gauze-based dressing. In certain embodiments, the foam material used in the first, skin contacting layer of the present disclosure is capable of absorbing 12 to 20 or more times its weight in would exudate, whereas the cotton gauze material employed in the manufacture of the prior art Unna boot constructions absorbs less than 2 times its weight in exudate.

Figure 5:
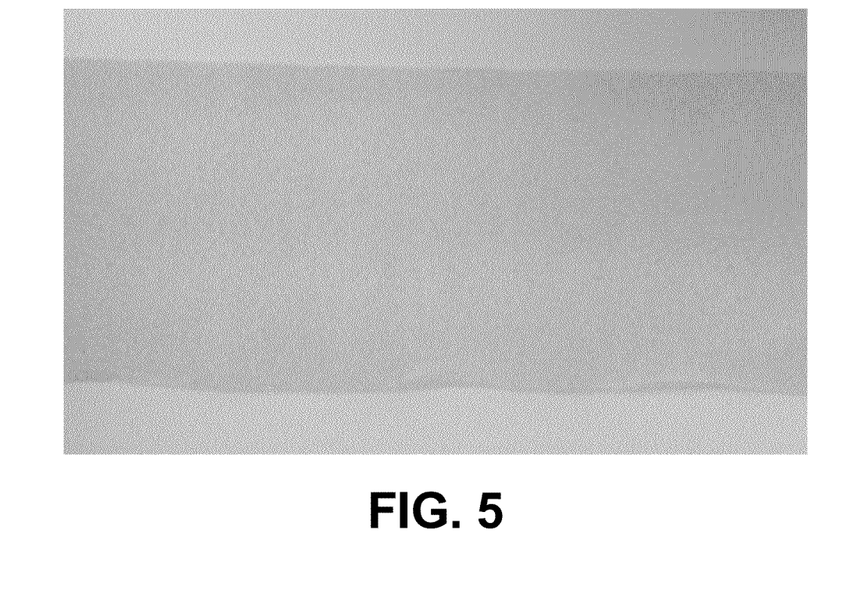
FIG. 5 is a top view of the foam layer according to one embodiment of the invention showing a relatively uniform distribution of the zinc oxide containing composition.
Figure 6:
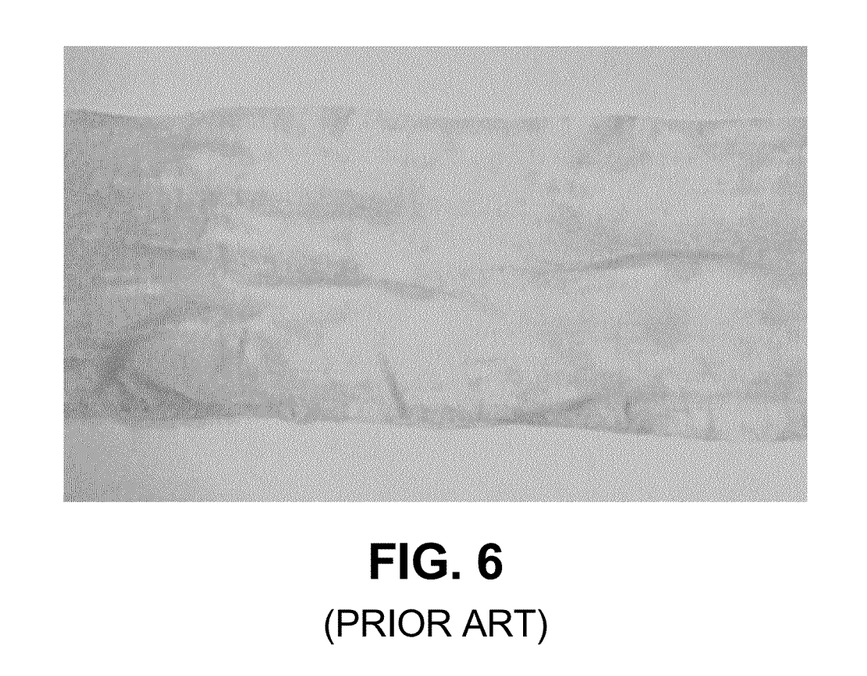
FIG. 6 is a top view of an exemplary prior art gauze dressing impregnated with an Unna boot formula, showing a relatively inconsistent distribution of the Unna paste.

Furthermore, it has been observed that the foam layer accepts and absorbs the zinc oxide containing composition with a much higher degree of uniformity than is found with the prior art Unna boot dressings. In comparing the present impregnated foam layer appearing in FIG. 5 with the prior art Unna boot gauze dressing appearing in FIG. 6, as well as the side-by-side images appearing in FIGS. 11A-11D wherein the foam layer of the present invention appears on the left and the prior art Unna boot gauze appears on the right, it can readily be seen that the zinc oxide containing composition is uniformly distributed on the foam substrate of the present bandage system; whereas, the prior art gauze contains varying uniformity, containing alternating regions of heavy and light coverage of Unna paste. The increased uniformity of the present development assures that an appropriate level of medication will be applied to the wound being treated.

Finally, in contrast to the prior art Unna boot gauze material which is rough and uneven, the impregnated foam layer herein provides enhanced comfort and softness relative to prior art Unna boot dressings. In addition, the pliability of the foam material in accordance with the present disclosure allows it to conform to most body parts without pleating, folding, or tucking, which can irritate and mark the underlying skin.

Figure 1:
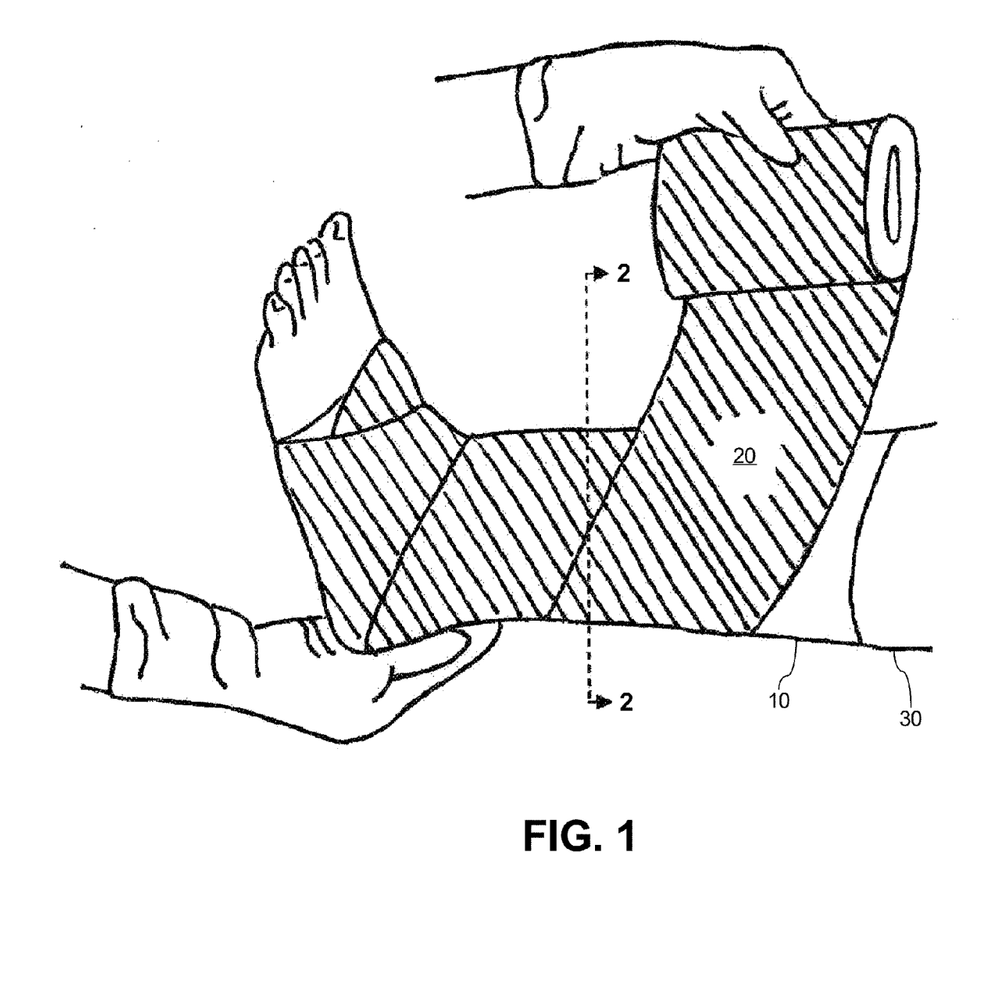
FIG. 1 is a depiction of a wound treatment system in accordance with an exemplary embodiment of the present invention.
Figure 2:
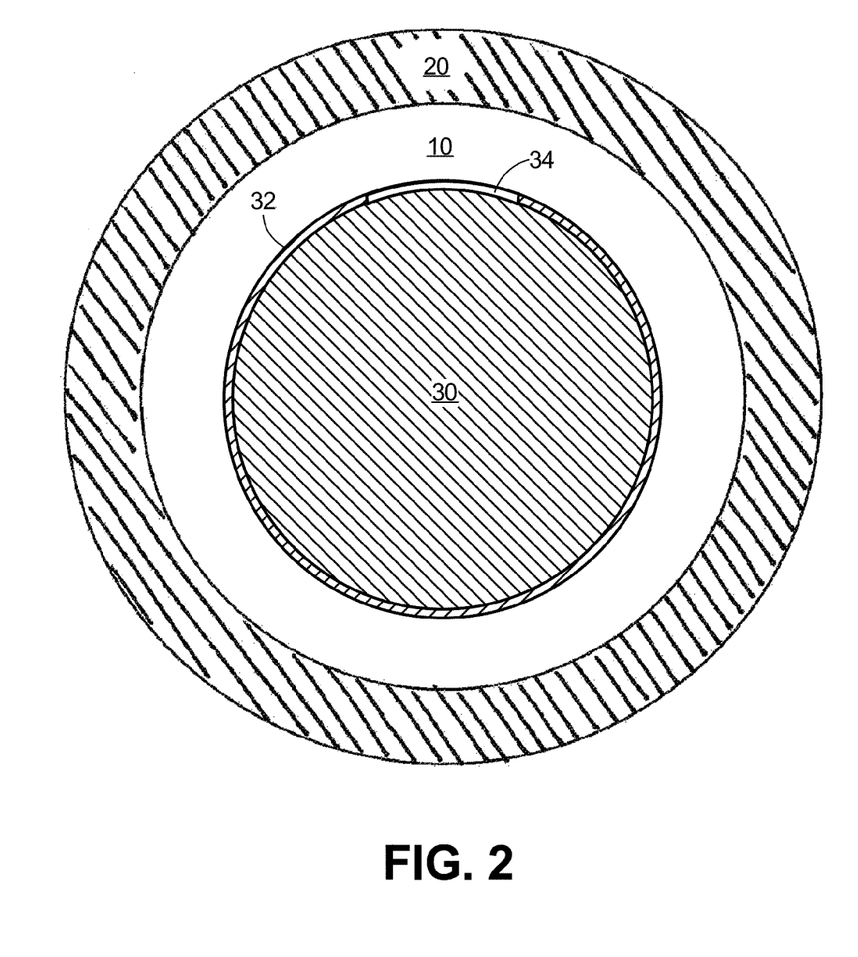
FIG. 2 is a cross-sectional view, taken along the lines 2-2 appearing in FIG. 1, showing an outer compression layer disposed on top of an inner foam layer impregnated with a zinc oxide containing composition, according to the depicted embodiment of the present invention.
Figure 3:
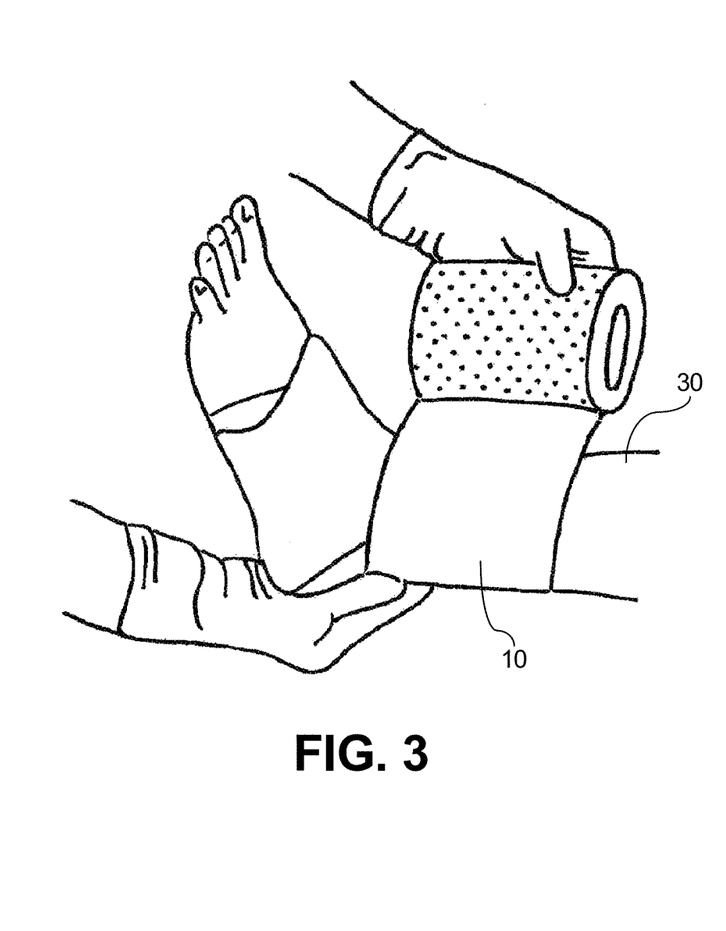
FIGS. 3, 10A, and 10B are depictions of an exemplary method herein for applying the foam layer impregnated with the zinc oxide containing composition to a patient's leg.
Figure 4:
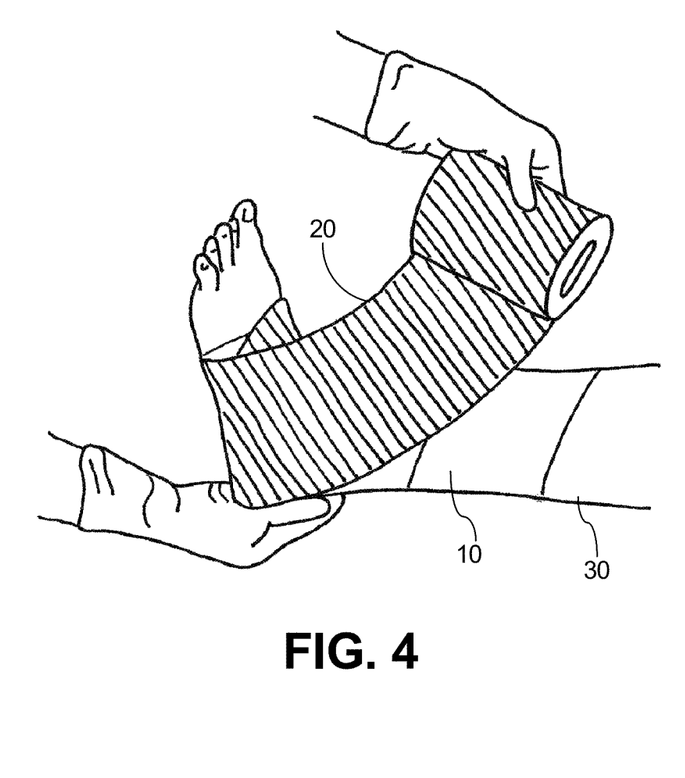
FIGS. 4 and 10C are depictions of an exemplary method for applying the second, compression layer on top of the foam layer.

FIGS. 1 and 2 depict one illustrative embodiment of the two-layer compression bandage system, as wrapped around a patient's leg 30 having one or more sores or ulcers 34 to be treated, as well as one or more regions of healthy skin 32. The wound bandaging system comprises an inner foam layer, generally designated 10, and a separate, outer, elastic compression layer, designated generally as 20.

The inner foam layer 10 is impregnated with a zinc oxide containing composition (with or without calamine and or ichthammol) and may include the presence of one or more additives or medications. Such additives or mediations may be in addition to or an alternative to a medication applied directly to the leg or wound prior to application of the bandage construction herein. Such additives or medications may include one or more antimicrobial agents which may be organic or inorganic, including for example, antibacterial and/or antifungal agents, anti-odor agents, anti-inflammatory agents including without limitation steroidal and non-steroidal anti-inflammatory agents, pain relieving agents, antibiotics or other medications, or any combinations of the foregoing. The zinc oxide containing composition may comprise from 0% to about 10% by weight of such additional additives or medications. The formulation may additionally include one or more aqueous or nonaqueous carriers, including without limitation, glycerin, gelatin, or other pharmaceutically acceptable carriers.

The anti-odor/agents may be substantially any appropriate material useful for the intended purpose of absorbing, neutralizing, or otherwise controlling odors. Anti-odor agents useful herein include but are not limited to activated carbon, cyclodextrins/modified cyclodextrins, activated alumina, metal powders, alumina silicates, metal oxides, zeolites, ceramics, diatomaceous earth, macroporous polymers, aerogels, cellulose and cellulosic derivatives, starches and starch derivatives, clay, talc, sodium bicarbonate, silicon dioxide, and combinations thereof.

The antimicrobial agents may be substantially any appropriate antimicrobial composition useful for the intended purpose of preventing or inhibiting the growth or reproduction of microbes, such as bacteria, fungi, viruses, or protozoa, for example, selected from Beta Hemolytic *Streptococci* (*Streptococcus pyogenes*), *Enterococci* (*Enterococcus faecalis*), *Staphylococci* (*Staphylococcus aureus*/MRSA), *Pseudomonas aeruginosa*, *Enterobacter* species, *Escherichia coli*, *Klebsiella* species, *Proteus* species, *Bacteroides* species, *Clostridium* species, *Candida* species, *Aspergillus* species.

In preferred embodiments, the antimicrobial agent may be inorganic metal based/organic antimicrobial agents or the like, although it will be recognized that the antimicrobial agent may other antimicrobial agents as known in the art, including antibiotics, antiseptics, antiviral agents, antifungal agents, and disinfectants. In especially preferred embodiments, the antimicrobial agent is silver nanoparticles or silver nitrate.

The antibiotic agent may be substantially any appropriate antibiotic useful for the intended purpose of killing or inhibiting the growth of microbes. The antibiotic may be selected from, for example, Methicillin, Neomycin sulfate, Bacitracin, Neomycin sulfate, and polymyxin B sulfate, etc.

The uniformity of the paste distribution over the foam layer 10 ensures that an adequate level of medication is applied to the wound region 34, while high absorbency of the foam layer 10 removes excess exudate which, if left in contact with the patient's leg 30 can have a deleterious effect on both the healthy skin 32 surrounding the wound 34, as well as on the wound itself.

One particular benefit of the present disclosure has been found in that the present system remains moist and pliable longer than the prior art Unna boot, which dries out and does not absorb exudate. While not intending to be bound by any particular theory, it is believed that this ability to remain moist results from the high degree of absorbency of the foam layer. In particular, it is believed that, during use, moisture evaporates from the impregnated foam layer and it begins to dry out. However, because of the high absorbency of the impregnated foam layer as compared to the prior art Unna boot gauze, this evaporation process leaves more room for the foam layer to absorb more wound exudate from the limb being treated. When this occurs, because the exudate itself is moist, the zinc oxide containing composition in the foam layer remains moist. It is believed that this process of evaporation and further exudate absorption continues allowing the foam layer to both remain moist and absorb a large quantity of exudate.

In use, the foam layer 10 is inherently elastic, that is, it can be deformed extensively and then substantially return to its original shape. Thus, the foam layer 10 can be wrapped with tension to impart some degree of compression on the patient's leg 30. An optional, second, compression layer 20 is wrapped over the foam layer 10 to enhance the compression exerted by the first layer 10.

Optionally, a third, outermost layer (not shown), such as a stocking, tube, sleeve, or the like, preferably a nylon stocking, may be provided and worn over the second layer, e.g., to provide a desired outward or cosmetic appearance of the bandage system.

Specific details of different kinds of useful foams and separate short or long stretch compression layers are described below.

The foam layer 10 impregnated with the zinc oxide containing composition, which may optionally include calamine and/or ichthammol, in the presence or absence of antimicrobial agent (organic or inorganic)) may be wound into a roll, e.g., for convenient storage and transport prior to use. In some embodiments, the foam layer comprises a cellular sheet material formed of a suitable material, such as chemically foamed or aerated plastic material, foamed rubber or a non-hardening cellulose sponge material. The foam layer may be formed of a generally open cell foam material or, alternately, a generally closed cell foam material. Preferably, the foam material used in the foam layer 10 is an open cell foam material, which allows exudate from the wound to be absorbed into the generally open or interconnected cellular network defined by the foam.

Open cell foams and closed cell foams are well known in the art, and those of ordinary skill in the art will recognize that foams termed "open cell" will naturally include some closed cells, and that foams termed "closed cell" will naturally include some open cells. Thus, as used herein, the terms "open cell" and "closed cell" do not imply that the foam must necessarily include 100% open or 100% closed cells. In general, most of the cells are closed off from each other in closed-cell foams. Open-cell foams have an interconnecting cell structure, are generally softer than closed-cell foams, and have less structural integrity than closed-cell foams.

In some embodiments, the foam material includes one or more of polyurethane, polyester, polyester/polyurethane, and polyethylene. The foam may have different weights, densities, and absorption capacities. For example, the foam may have a weight of from about 75 g/cm² ($1.07 \times 10^{-4}$ lb/in²) to 95 g/cm² ($1.35 \times 10^{-4}$ lb/in²) or 45 g/m² ($0.61 \times 10^{-4}$ lb/in²) to 125 g/m² ($1.82 \times 10^{-4}$ lb/in²). In particular embodiments, the foam has a weight of about 34 g/m² ($0.46 \times 10^{-4}$ lb/in²). When constructed of polyurethane, the foam generally has a density of about 23 kg/m³ (1.5 lb/ft³) to 29 kg/m³ (1.9 lb/ft³) or 13 kg/m³ (0.9 lb/ft³) to 39 kg/m³ (2.6 lb/ft³), e.g., about 26 kg/m³ (1.7 lb/ft³). The foam may have a thickness between about 0.15 cm (0.06 in) and 0.45 cm (0.18 in), for example, between about 0.27 cm (0.11 in) and 0.33 cm (0.13 in). The foam may be of any thickness desired for a particular application, such as the severity of the wound, whether the patient intends to wear the bandage system under clothing or shoes, the volume of exudate exhibited by the ulcer(s) to be treated, the length of time the bandage system will be left on the leg or the frequency at which the bandage system will be changed, and so forth.

In some embodiments, the foam layer is a thin-gauge sheet of polyurethane or polyester/polyurethane foam material having a thickness of about 0.30 cm (0.12 in). In some embodiments, the foam layer comprises an elongate strip about 3-4 inches wide and approximately 5-10 yards in length. One suitable polyurethane foam sheeting material type is manufactured and sold by William T. Burnett & Co. (Jessup, Md.) under the product identifier S82HD. This foam sheeting has a density of about 26 g/m³ (1.7 lb/ft³), a minimum tensile strength of 159 kPa (23 lb/in² or psi) and an average tensile strength of 207 kPa (30 psi), a minimum tear resistance of 525 N/m (3.00 lb/in-linear or pli) and an average tear resistance of 700 N/m (4.00 pli), and a minimum elongation of 300% and an average elongation of 450%, as determined by using the ASTM-D3574 standard methods of testing flexible cellular materials-slab, bonded, and molded urethane foam. The S82HD polyester/polyurethane foam further has a minimum compression force of 2.8 kN/m² (0.40 psi) and an average compression force of 3.4 kN/m² (0.50 psi) at 25% deflection, and a minimum compression force of 3.1 kN/m² (0.45 psi) and an average compression force of 4.1 kN/m² (0.60 psi) at 50% deflection.

The S82HD polyester/polyurethane foam having a thickness of 0.3 cm (0.12 in) produces a layer with satisfactory cohesive and cushioning properties; however, other thicknesses, e.g., up to 0.5 cm (0.20 in) or even greater, may be employed to provide additional cushioning.

As noted above, the inner foam layer may be formed of an elastic foam sheet material with some degree of stretch, to provide some degree of compression of the affected limb. In alternative embodiments, however, it will be recognized that is not necessary that the inner foam layer provide an appreciable level compression of the affected limb and even without significant compression, the foam layer serves to provide cushioning, exudate absorption, comfort, and uniform application of the zinc oxide containing composition without compression, wherein compression of the affected limb is provided by the outer layer 20. However, in certain alternative embodiments, it is contemplated that the inner foam layer could be wrapped under light tension to provide some initial degree of compression.

In some embodiments, the outer layer 20 is a "short stretch" elastic bandage and preferably a short stretch cohesive elastic bandage, which cohesively bonds to itself when wrapped in overlapping fashion, thus eliminating the need for bandage clips or other bandage fasteners. As used herein, the term "short stretch" refers to a bandage which is able to stretch, e.g., approximately 25% to 80% beyond its original, unstretched length. Unlike "long stretch" articles, which are able to stretch from approximately 100% up to several times beyond their original length in the longitudinal direction and thereby provide constant pressure at rest and work, i.e., a low static stiffness index (SSI), short stretch bandages are able to provide more effective compression through a low resting pressure and a high standing or working pressure, i.e., a high SSI, e.g., greater than about 10 mm Hg. The use of a low stretch compression bandage as the outer layer is especially advantageous for patients with venous insufficiency, since the low resting pressure provides comfort when the patient is recumbent while also preventing expansion of muscle diameter while the patient is ambulatory, thereby increasing venous and lymphatic return when the muscles of the leg contract.

In certain embodiments, the elastic compression layer 20 may be a latex-free cohesive elastic bandage, as disclosed in U.S. Pat. No. 6,156,424, the entire contents of which are incorporated herein by reference. In yet further embodiments, the elastic compression layer 20 may be a layer that eliminates the need for bandage scissors by facilitating hand tearing, as disclosed in U.S. Pat. No. 5,762,623, the entire contents of which are incorporated by reference herein. In still further embodiments, the separate elastic compression layer 20 may be a layer that provides extraordinary cohesive-like interaction with the foam layer 10 by comprising a warp-knit weft-insertion fabric, also disclosed in U.S. Pat. No. 5,762,623.

One suitable separate elastic compression layer that features all of the above advances is manufactured and sold by Andover Healthcare, Inc. (Salisbury, Mass.) under the trade designation "Co-Flex® NL." Co-Flex® NL is intended for controlled compression that will not constrict over time, i.e., a short-stretch bandage. In addition to its fabric-based dimensional stability and protection from dirt and moisture, Co-Flex® NL is porous, lightweight, and cohesive yet easy to remove.

Figure 7:
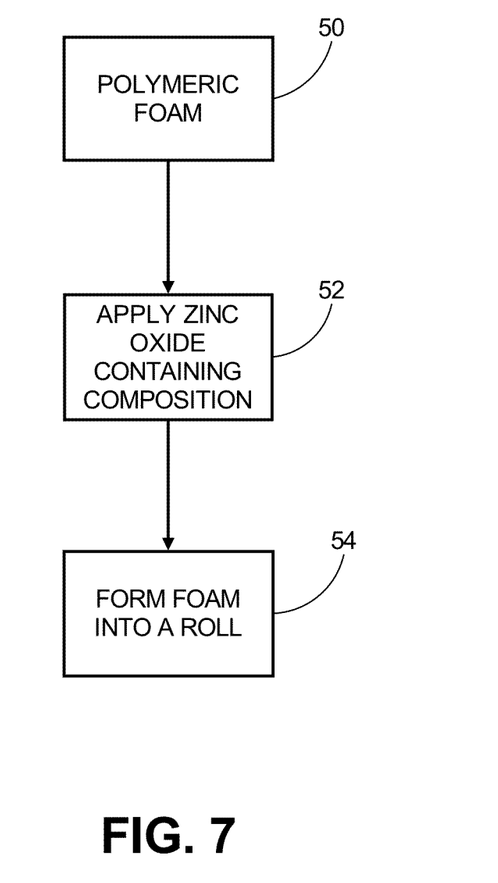
FIG. 7 is a flowchart depicting an exemplary process for fabricating the foam layer impregnated with the zinc oxide containing composition.

A flowchart for preparing the foam layer 10 impregnated with the zinc oxide containing composition is shown in FIG. 7. In this embodiment, foam is provided at step 50 and is impregnated with a zinc oxide containing composition at step 52, e.g., by dipping the foam in a bath containing the zinc oxide containing composition. The dipped foam layer 10 with the zinc oxide containing composition may advantageously then be formed into a roll at step 54.

Figure 8:
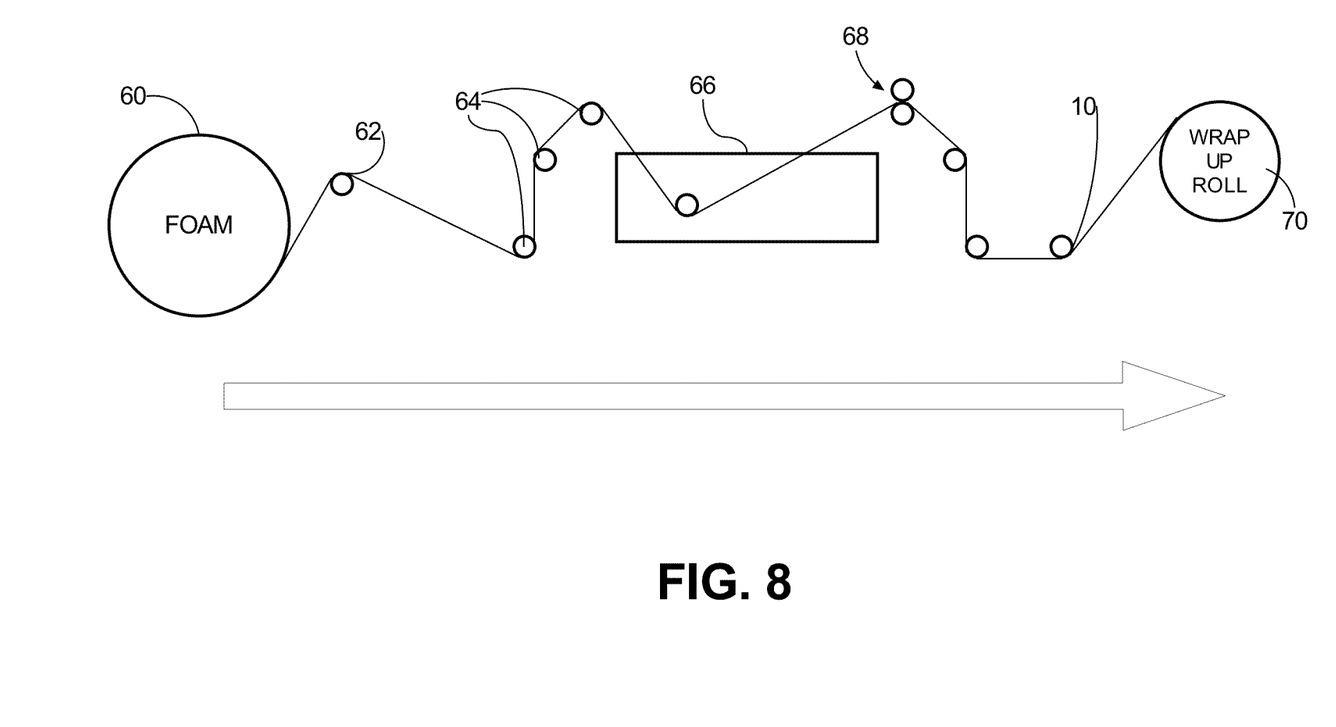
FIG. 8 is a schematic illustration of an apparatus and process for fabricating the foam layer impregnated with the zinc oxide containing composition according to an exemplary embodiment.

An illustrative apparatus and process for preparing the foam layer 10 impregnated with a zinc oxide containing composition is shown schematically in FIG. 8. The apparatus includes a feed roll 60 for supplying the unimpregnated foam 62. The foam 62 is guided into nip rolls 64, which steady the foam and direct the foam through a bath or tank 66 containing the zinc oxide containing composition. The impregnated foam passes through squeegee rollers 68 (or alternatively, squeegees, blades, an air knife, or the like) to remove excess zinc oxide containing composition to provide a foam article 10 that is impregnated with a desired amount of the zinc oxide containing composition.

The amount of the zinc oxide containing composition applied to the foam layer 10 may be, for example, between about 250 g/m² and 500 g/m², preferably between about 300 g/m² and 400 g/m², and more preferably between about 340 g/m² and 370 g/m², although it will be recognized that the zinc oxide containing composition may be applied in any amount desired for a particular application. Then, in some embodiments, the finished product is wound into a take-up roll 70. The take-up roll 70 can then be used directly or rewound into a finished roll of any desired length, width, and winding tension.

Figure 9:
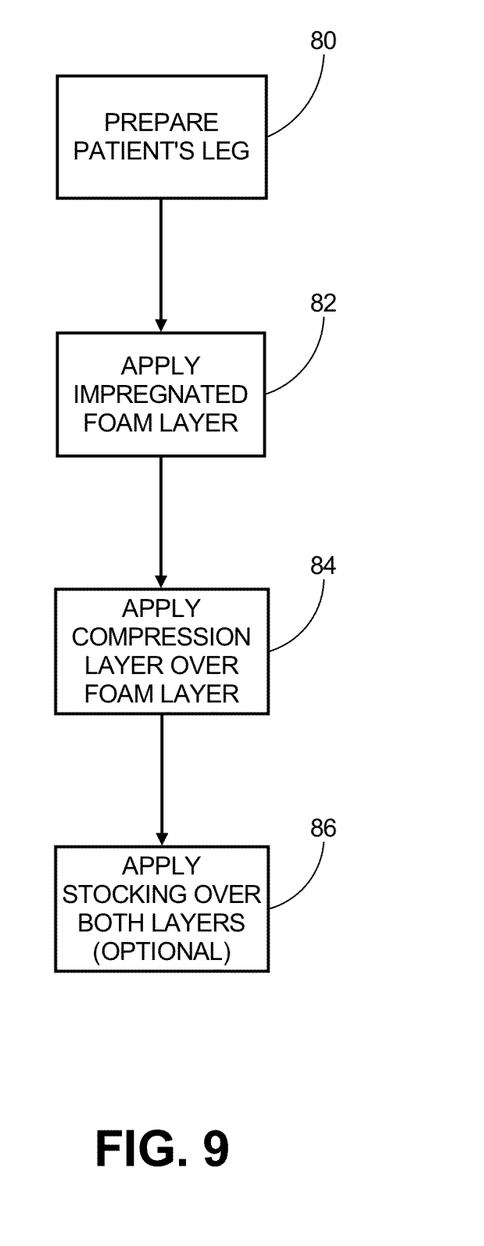
FIG. 9 is a flowchart depicting a method for using the wound treatment system according to an exemplary embodiment.
Figure 10A:
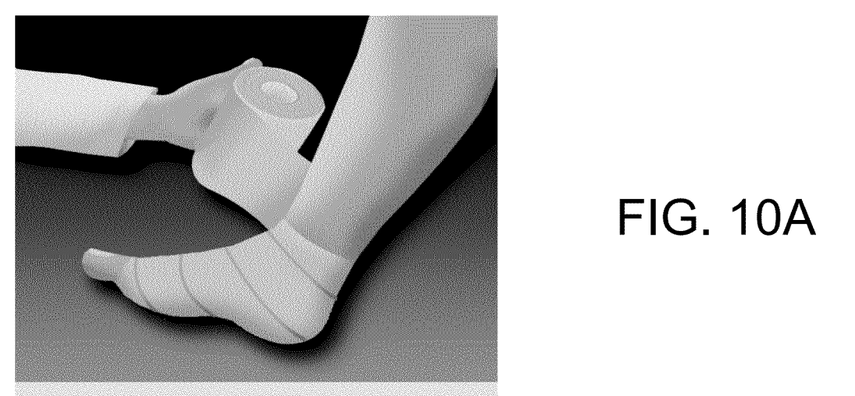
Figure 10B:
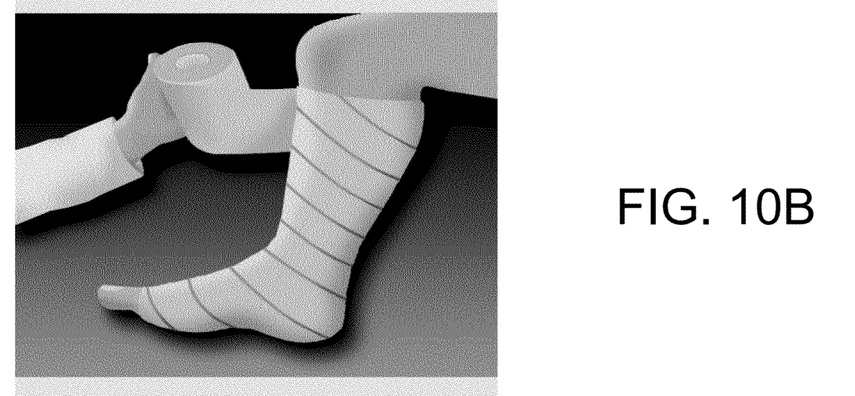
Figure 10C:
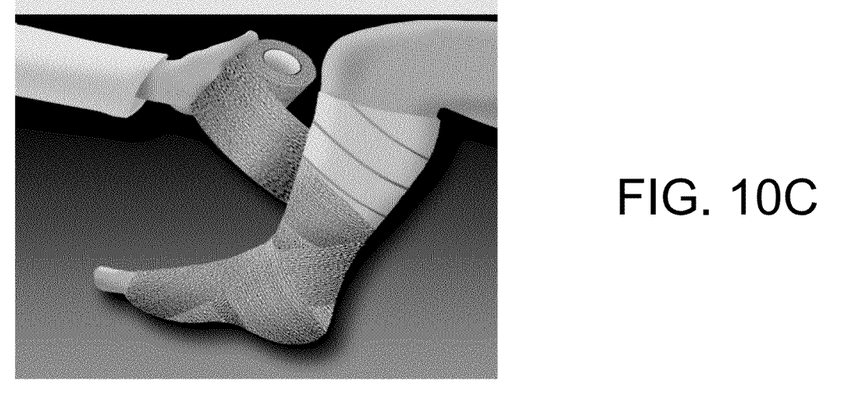
Figure 11A:
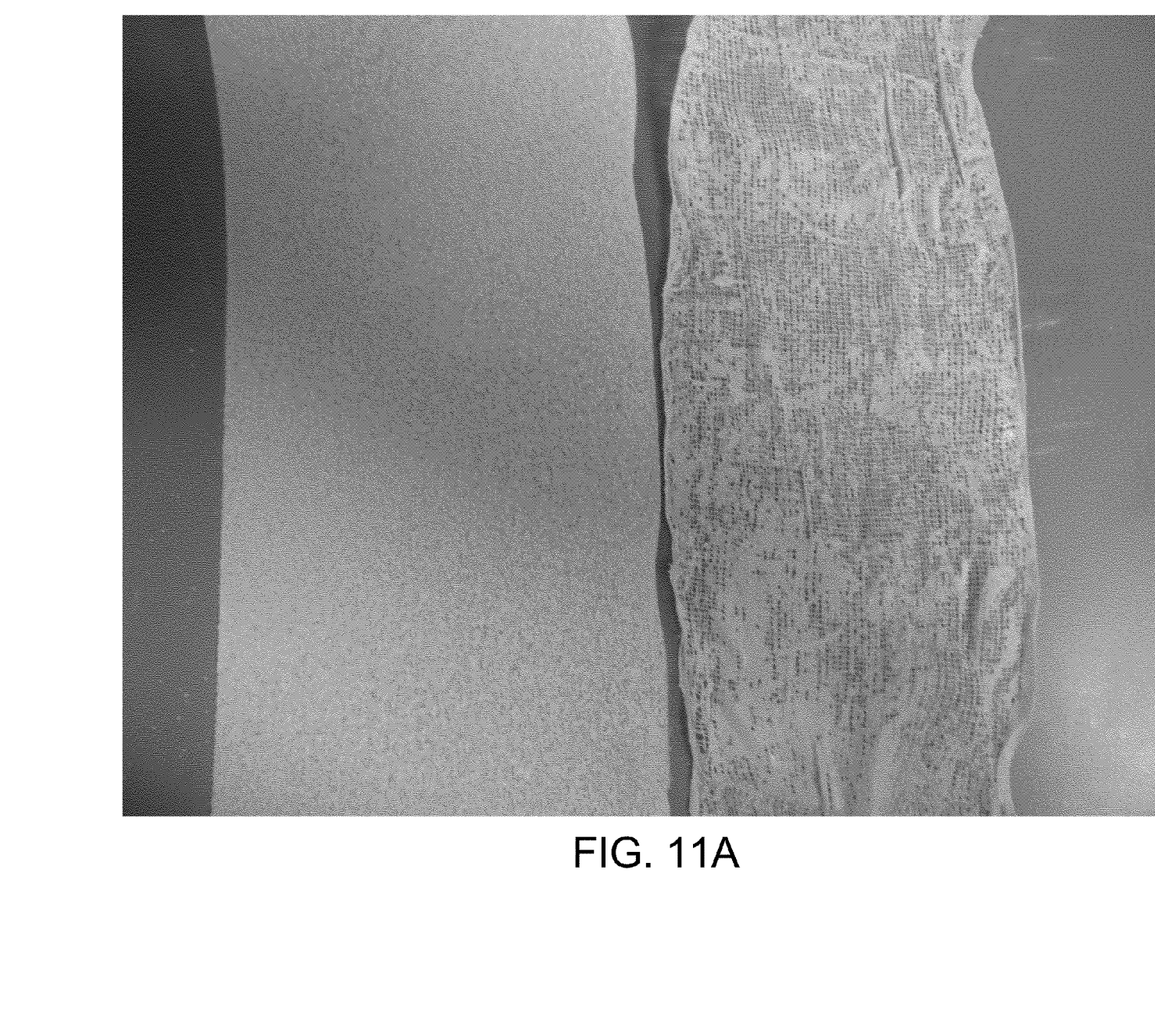
FIGS. 11A-11D are several side-by-side images comparing the uniformity of coverage of the zinc oxide containing composition in the presently disclosed impregnated foam dressing layer (appearing on the left side of the images) with the prior art Unna boot impregnated gauze dressing (appearing on the right side of the images).
Figure 11B:
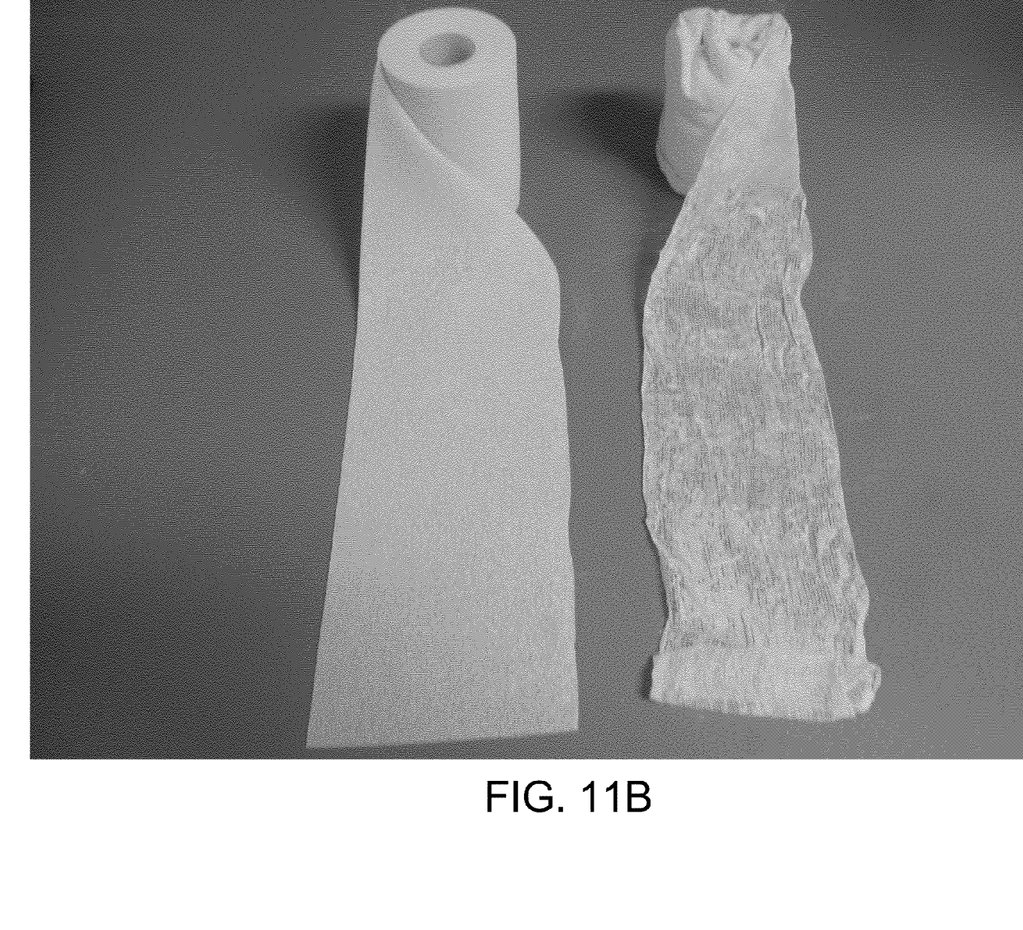
Figure 11C:
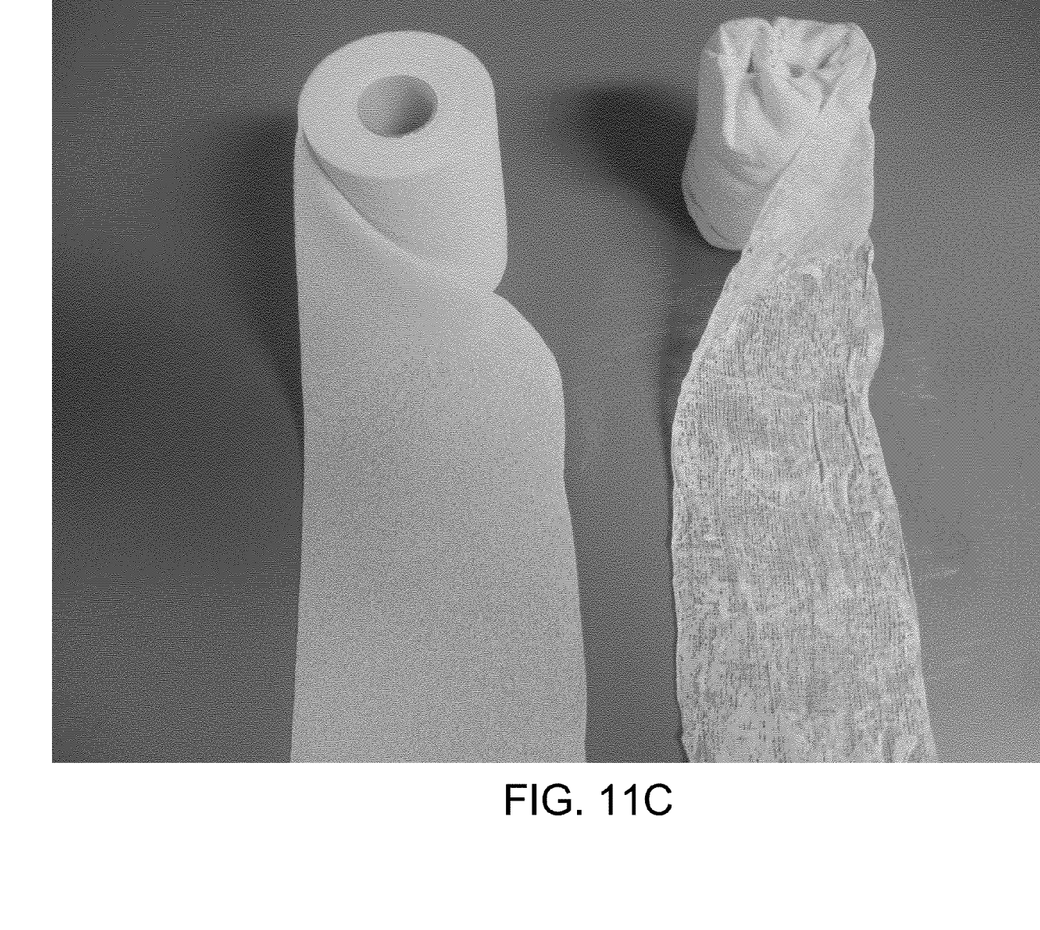
Figure 11D:
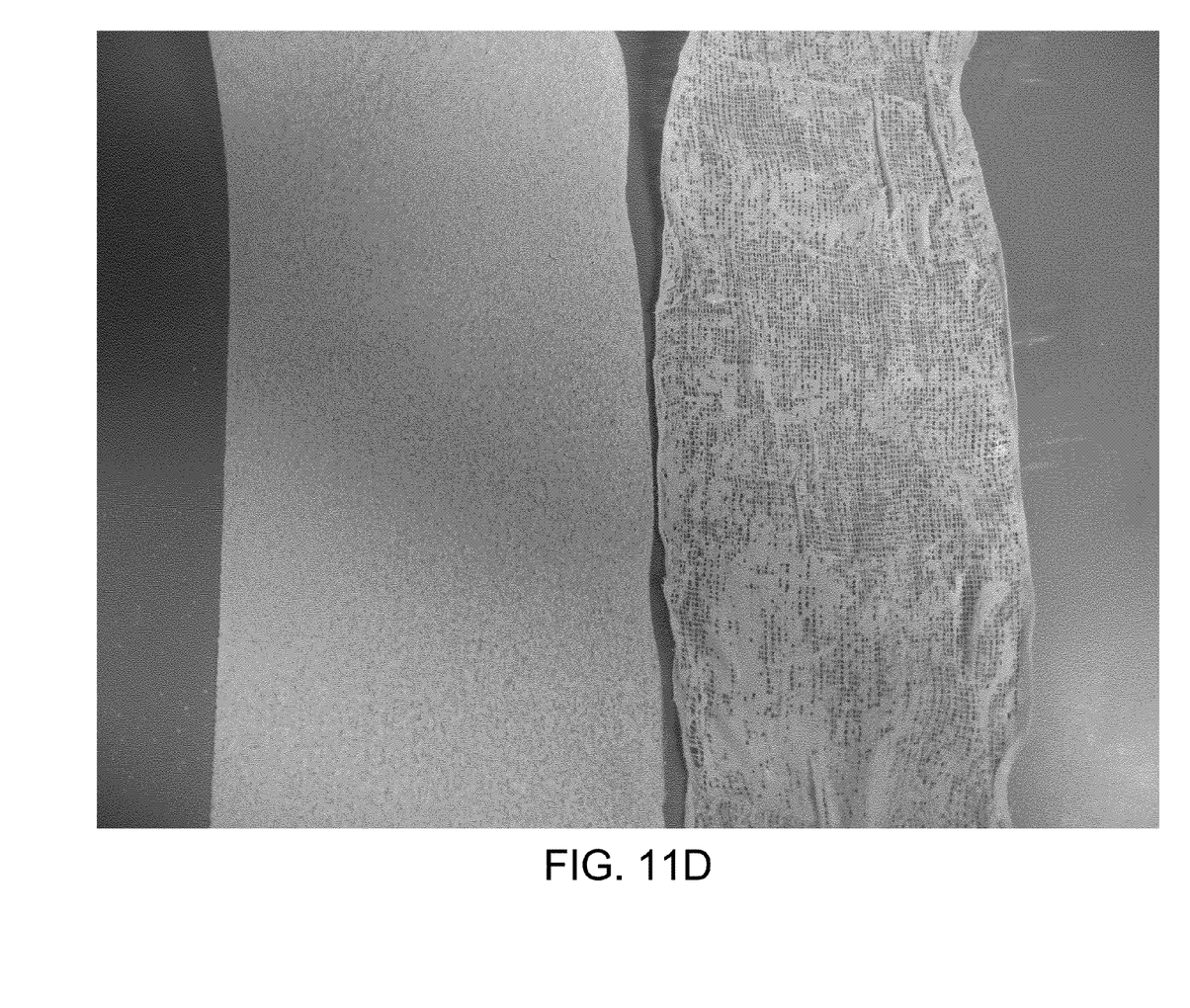

Tests were performed to compare the absorbency of the present foam system with the absorbency of the prior art Unna boot gauze material. The prior art material tested was the GELOCAST® Unna boot, which is commercially available from BSN Medical, Inc. The results of the absorbency testing for the GELOCAST sample are summarized below in Table 1.

technique, e.g., with 50-75% overlap, is one option here. The layer 10 may be wrapped with light tension to provide an initial degree of compression to the patient's leg 30. In typical applications, the foam layer 10 will be applied beginning at the base of the patient's toes, and ending 1-2 inches below the patient's knee.

At step 84, the optional separate elastic compression layer 20 is disposed directly on top of the foam layer 10. Again, a simple spiral wrapping technique with, e.g., 50-75% overlap, is one option. Optionally, at step 86, a stocking, sleeve, etc., e.g., formed of nylon, may be used to cover the combined two-layer bandage system, e.g., for a smooth outer surface and an improved cosmetic appearance.

The description above should not be construed as limiting the scope of the invention, but as merely providing illustra-

TABLE 1

| Sample | Thickness of Fabric | Volume of Fabric | Weight of Fabric (Dry) | Weight of Fabric (Wet) | Weight of Water | Density of Fabric | Absorbency = Weight of Water/Weight of Fabric | Swell (%) |
|---|---|---|---|---|---|---|---|---|
| GELOCAST Fabric Sample #1 | 0.010 in (0.025 cm) | 0.000023 ft³ (0.65 cm³) | 0.000197 lbs (0.0894 g) | 0.0007 lbs (0.3 g) | 0.0005 lbs (0.2 g) | 8.51 lbs/ft³ (0.136 g/cm³) | 2.75 | — |
| GELOCAST Fabric Sample #2 | 0.011 in (0.028 cm) | 0.000025 ft³ (0.71 cm³) | 0.000202 lbs (0.0916 g) | 0.0007 lbs (0.3 g) | 0.0005 lbs (0.2 g) | 7.93 lbs/ft³ (0.127 g/cm³) | 2.59 | — |
| GELOCAST Fabric Average | 0.011 in (0.27 cm) | 0.000024 ft³ (0.68 cm³) | 0.000200 lbs (0.0907 g) | 0.0007 lbs (0.3 g) | 0.0005 lbs (0.2 g) | 8.22 lbs/ft³ (0.132 g/cm³) | 2.67 | — |

Absorbency testing for the foam layer was conducted on 50 mil thick foam available from William T. Burnett & Co. of Jessup, Md. The results of the absorbency test for the foam material are summarized in Table 2 below.

tions to some of the presently preferred embodiments of this invention. In light of the above description and examples, various other modifications and variations will now become apparent to those skilled in the art without departing from the

TABLE 2

| Sample | Thickness of Foam | Volume of Foam | Weight of Foam (Dry) | Weight of Foam (Wet) | Weight of Water | Density of Foam | Absorbency = Weight of Water/Weight of Foam | Swell (%) |
|---|---|---|---|---|---|---|---|---|
| Burnett Foam Sample #1 | 0.057 in (0.014 cm) | 0.000132 ft³ (3.74 cm³) | 0.000181 lbs (0.0821 g) | 0.0037 lbs (1.7 g) | 0.0035 lbs (1.6 g) | 1.37 lbs/ft³ (0.0219 g/cm³) | 19.54 | L = 0.0 W = 3.1 |
| Burnett Foam Sample #2 | 0.055 in (0.014 cm) | 0.000127 ft³ (3.60 cm³) | 0.000176 lbs (0.0798 g) | 0.0039 lbs (1.8 g) | 0.0038 lbs (1.7 g) | 1.38 lbs/ft³ (0.0221 g/cm³) | 21.39 | L = 0.0 W = 3.1 |
| Burnett Foam Average | 0.056 in (0.014 cm) | 0.000130 ft³ (3.68 cm³) | 0.00079 lbs (0.0812 g) | 0.0038 lbs (1.7 g) | 0.0037 lbs (1.7 g) | 1.38 lbs/ft³ (0.0220 g/cm³) | 20.46 | L = 0.0 W = 3.1 |

Figure 12:
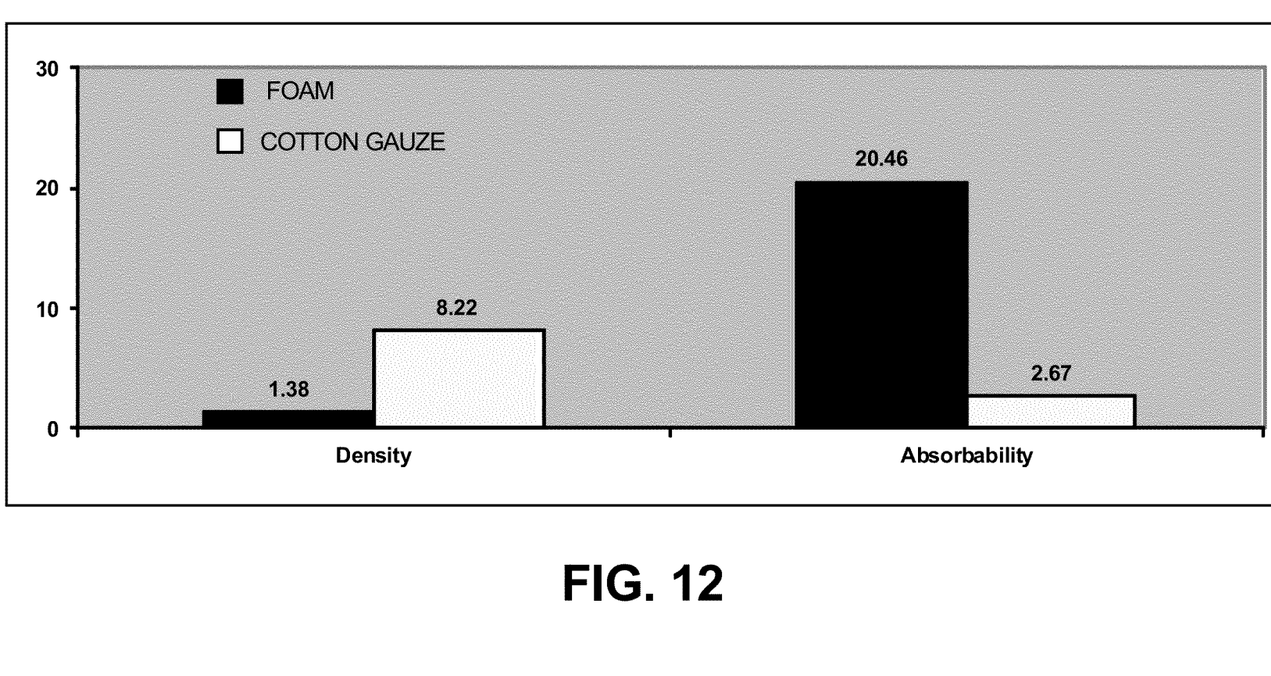
FIG. 12 is a chart illustrating the respective densities and absorbabilities of the gauze fabric material used in connection with the prior art Unna boot constructions and the foam layer used in connection with the present bandage system.

A chart illustrating the respective densities and absorbencies of the present foam material and the prior art gauze fabric material is illustrated in FIG. 12.

An illustrative method for using the wound bandage system in accordance with this disclosure is described by the flowchart appearing in FIG. 9. The method involves cleaning and preparing the patient's leg for use of a bandage or wrap at step 80. For example, the skin may be cleansed and, if necessary, the wound may be debrided. Optionally, a skin lubricant may be applied to the normal skin of the leg, if desired. Also, if desired, any other ointment or medication, such as a topical corticosteroid to control chronic inflammation around the wound, a topical antibacterial agent, etc. may be applied to the leg.

At step 82, the impregnated foam layer 10 is applied directly to the patient's leg 30. A simple spiral wrapping spirit and scope of the present invention as defined by the appended claims. Accordingly, the scope of the invention should be determined solely by the appended claims and their legal equivalents.

What is claimed is:

1. A wound care device for treatment of wounds on a limb of a subject, said device comprising:
    an inner, skin contacting layer formed of an elongate strip of a foam material, said foam material impregnated with a zinc oxide containing composition comprising zinc oxide in a pharmaceutically acceptable carrier, wherein said zinc oxide containing composition comprises zinc oxide, calamine, water, glycerin, gelatin, sorbitol, magnesium aluminum silicate, and Paraben-DU.

2. The device according to claim 1, further comprising an outer layer comprising an elastic compression bandage disposed over the skin contacting layer.

3. The device of claim 2, wherein said outer layer is stretchable to provide a compressive force when stretched and wrapped about the limb of the subject.

4. The device of claim 3, wherein said outer layer has an unstretched length and a maximum stretched length, wherein the maximum stretched length is about 40-80% greater than the unstretched length.

5. The device of claim 2, wherein said outer layer is a cohesive elastic bandage.

6. The device of claim 2, further comprising:
a sleeve adapted to be worn over said outer layer.

7. The device according to claim 1, wherein said zinc oxide containing composition contains from about 5% to about 40% by weight of zinc oxide.

8. The device according to claim 1, further comprising:
said skin contacting layer having a thickness of between about 0.15 cm and about 0.45 cm.

9. The device according to claim 1, wherein said foam material is formed of a polymeric foam material selected from polyurethane, polyester, polyester/polyurethane, and polyethylene.

10. The device according to claim 1, wherein said zinc oxide containing composition contains up to about 10% by weight of calamine.

11. The device according to claim 1, wherein said zinc oxide containing composition contains up to about 10% by weight of ichthammol.

12. The device of claim 1, wherein said zinc oxide containing composition further comprises an additive selected from: one or more organic antimicrobial agents, one or more inorganic antimicrobial agents, one or more anti-odor agents, one or more anti-inflammatory agents, one or more pain relieving agents, one or more antibiotics, and any combination thereof.

13. The device of claim 1, wherein said skin contacting layer is stretchable to provide a compressive force when stretched and wrapped about the limb of the subject.

14. The device of claim 1, further comprising:
a sleeve adapted to be worn over said skin contacting layer.

15. A method for treating a skin ulcer in a limb of a subject in need thereof, said method comprising the steps of:
circumferentially wrapping an inner, skin-contacting layer around the limb, the inner layer directly contacting the limb, the inner layer characterized by an elongate sheet of a foam material impregnated with a zinc oxide containing composition, wherein said zinc oxide containing composition comprises zinc oxide, calamine, water, glycerin, gelatin, sorbitol, magnesium aluminum silicate, and Paraben-DU.

16. The method of claim 15, further comprising:
circumferentially wrapping a separate outer layer around the limb over the skin-contacting layer, the outer layer comprising an elastic compression bandage.

17. The method of claim 16, wherein said outer layer is stretchable to provide a compressive force when stretched and wrapped about the limb of the subject.

18. The method of claim 17, wherein said outer layer has an unstretched length and a maximum stretched length, wherein the maximum stretched length is about 40-80% greater than the unstretched length.

19. The method of claim 16, wherein said outer layer is a cohesive elastic bandage.

20. The method of claim 16, further comprising:
applying a third layer over said compression bandage layer, said third layer selected from a stocking and a sleeve.

21. The method according to claim 15, wherein said zinc oxide containing composition contains from about 5% to about 40% by weight of zinc oxide.

22. The method according to claim 15, wherein said skin contacting layer has a thickness of between about 0.15 cm and about 0.45 cm.

23. The method according to claim 15, wherein said foam material is formed of a polymeric foam material selected from polyurethane, polyester, polyester/polyurethane, and polyethylene.

24. The method according to claim 15, wherein said zinc oxide containing composition contains up to about 10% by weight of calamine.

25. The method according to claim 15, wherein said zinc oxide containing composition contains up to about 10% by weight of ichthammol.

26. The method of claim 15, wherein said zinc oxide containing composition further comprises an additive selected from one or more organic antimicrobial agents, one or more inorganic antimicrobial agents, one or more anti-odor agents, one or more anti-inflammatory agents, one or more pain relieving agents, one or more antibiotics, or any combination thereof.

27. The method of claim 15, wherein said skin-contacting layer is stretchable to provide a compressive force when stretched and wrapped about the limb of the subject.

28. A kit having component parts packaged together, said kit comprising:
a first, skin-contacting layer, said inner layer characterized by an elongate, strip of a foam material impregnated with a zinc oxide containing composition, wherein said zinc oxide containing composition comprises zinc oxide, calamine, water, glycerin, gelatin, sorbitol, magnesium aluminum silicate, and Paraben-DU; and
a second layer comprising an elastic, compression bandage.

29. The kit of claim 28, further comprising:
a third layer selected from a stocking and a sleeve, the third layer adapted to be received over the second layer.

30. The kit of claim 28, wherein said zinc oxide containing composition contains from about 5% to about 40% by weight of zinc oxide.

31. The kit of claim 28, wherein said foam material is formed of a polymeric foam material selected from polyurethane, polyester, polyester/polyurethane, and polyethylene.

* * * * *